United States Patent
Khait et al.

(10) Patent No.: US 9,585,543 B2
(45) Date of Patent: Mar. 7, 2017

(54) DEVICE AND SYSTEM FOR CHECKING THE STATUS OF AN IN-VIVO IMAGING DEVICE

(71) Applicant: GIVEN IMAGING LTD., Yoqneam (IL)

(72) Inventors: Semion Khait, Tiberias (IL); Ido Bettesh, Zichron Ya'akov (IL)

(73) Assignee: GIVEN IMAGING LTD., Yoqneam (IL)

(*) Notice: Subject to any disclaimer, the term of this patent is extended or adjusted under 35 U.S.C. 154(b) by 0 days.

(21) Appl. No.: 14/797,219

(22) Filed: Jul. 13, 2015

(65) Prior Publication Data

US 2015/0313448 A1 Nov. 5, 2015

Related U.S. Application Data

(63) Continuation of application No. 11/723,501, filed on Mar. 20, 2007, now Pat. No. 9,084,547.
(Continued)

(51) Int. Cl.
*A61B 1/00* (2006.01)
*A61B 1/04* (2006.01)
(Continued)

(52) U.S. Cl.
CPC ........ *A61B 1/00055* (2013.01); *A61B 1/0002* (2013.01); *A61B 1/00009* (2013.01);
(Continued)

(58) Field of Classification Search
CPC . A61B 1/041; A61B 1/00016; A61B 1/00032; A61B 1/00034; A61B 1/00036;
(Continued)

(56) References Cited

U.S. PATENT DOCUMENTS 2,216,974 A 10/1940 Hogan
3,146,326 A 8/1964 Thorne
(Continued)

FOREIGN PATENT DOCUMENTS

DE 3440177 5/1986
JP 57-45833 3/1982
(Continued)

OTHER PUBLICATIONS

U.S. Appl. No. 10/493,751, filed Apr. 27, 2004, Glukhovsky et al.
(Continued)

*Primary Examiner* — Anhtuan T Nguyen
*Assistant Examiner* — William Chou
(74) *Attorney, Agent, or Firm* — Pearl Cohen Zedek Latzer Baratz LLP

(57) ABSTRACT

A device and system for monitoring the status of a battery in an in-vivo imaging device, prior to use of the in-vivo imaging device. The device may include a frame counter for counting the number of frames captured and may include monitoring the voltage of the battery. A warning signal is generated if it is determined that the battery is faulty prior to use. The warning signal can be generated by the device and/or by a receiver which receives data from the in-vivo imaging device and/or a by workstation which receives the data from the receiver.

8 Claims, 1 Drawing Sheet

Related U.S. Application Data

(60) Provisional application No. 60/787,187, filed on Mar. 30, 2006.

(51) Int. Cl.
*A61B 1/06* (2006.01)
*A61B 5/06* (2006.01)

(52) U.S. Cl.
CPC ...... *A61B 1/00016* (2013.01); *A61B 1/00032* (2013.01); *A61B 1/00045* (2013.01); *A61B 1/00156* (2013.01); *A61B 1/041* (2013.01); *A61B 5/06* (2013.01)

(58) Field of Classification Search
CPC .............. A61B 1/0684; A61B 8/4472; A61B 2560/0209
USPC ................. 600/109, 117, 118, 160, 424, 407
See application file for complete search history.

(56) References Cited

U.S. PATENT DOCUMENTS

| | | | |
|---|---|---|---|
| 3,683,389 A | | 8/1972 | Hollis |
| 3,971,362 A | | 7/1976 | Pope et al. |
| 4,278,077 A | | 7/1981 | Mizumoto |
| 4,689,621 A | | 8/1987 | Kleinberg |
| 4,741,327 A | | 5/1988 | Yabe |
| 4,844,076 A | | 7/1989 | Lesho et al. |
| 5,070,357 A | * | 12/1991 | Kazami ............... G03B 17/18 396/279 |
| 5,279,607 A | | 1/1994 | Schentag et al. |
| 5,400,267 A | | 3/1995 | Denen et al. |
| 5,604,531 A | | 2/1997 | Iddan et al. |
| 5,609,561 A | | 3/1997 | Uehara et al. |
| 5,819,736 A | | 10/1998 | Avny et al. |
| 5,967,969 A | | 10/1999 | Enomoto et al. |
| 5,993,378 A | | 11/1999 | Lemelson |
| 6,204,746 B1 | | 3/2001 | Kane et al. |
| 6,240,312 B1 | | 5/2001 | Alfano et al. |
| 6,436,032 B1 | | 8/2002 | Eto et al. |
| 6,516,227 B1 | | 2/2003 | Meadows et al. |
| 6,632,175 B1 | | 10/2003 | Marshall |
| 6,709,387 B1 | | 3/2004 | Glukhovsky et al. |
| 6,712,756 B1 | | 3/2004 | Kura et al. |
| 7,009,634 B2 | | 3/2006 | Iddan et al. |
| 7,914,442 B1 | * | 3/2011 | Gazdzinski ......... A61B 1/00009 600/109 |
| 8,496,657 B2 | * | 7/2013 | Bonutti ............... A61B 17/0401 606/62 |
| 2001/0017649 A1 | | 8/2001 | Yaron |
| 2001/0041825 A1 | | 11/2001 | Shibata et al. |
| 2001/0051766 A1 | | 12/2001 | Gazdzinski |
| 2002/0103417 A1 | | 8/2002 | Gazdinski |
| 2002/0198439 A1 | | 12/2002 | Mizumo |
| 2003/0043263 A1 | | 3/2003 | Glukhovsky et al. |
| 2003/0107652 A1 | * | 6/2003 | Williams ............ A61B 1/00177 348/207.99 |
| 2003/0114742 A1 | | 6/2003 | Lewkowicz et al. |
| 2003/0117491 A1 | | 6/2003 | Avni et al. |
| 2003/0171648 A1 | | 9/2003 | Yokoi et al. |
| 2003/0171649 A1 | | 9/2003 | Yokoi et al. |
| 2003/0171652 A1 | | 9/2003 | Yokoi et al. |
| 2004/0027459 A1 | | 2/2004 | Segawa et al. |
| 2004/0073087 A1 | | 4/2004 | Glukhovsky et al. |
| 2004/0087832 A1 | | 5/2004 | Glukhovsky |
| 2004/0138552 A1 | | 7/2004 | Harel et al. |
| 2004/0150958 A1 | * | 8/2004 | Calhoon .............. H05K 5/0208 361/725 |
| 2005/0261552 A1 | | 11/2005 | Mori |
| 2006/0178557 A1 | * | 8/2006 | Mintchev ............ A61B 1/041 600/104 |
| 2006/0224063 A1 | | 10/2006 | Segawa et al. |
| 2006/0252986 A1 | | 11/2006 | Akagi et al. |
| 2007/0255087 A1 | | 11/2007 | Minai |
| 2007/0268280 A1 | * | 11/2007 | Fujita ................. A61B 1/00045 345/204 |
| 2008/0108868 A1 | | 5/2008 | Swain et al. |
| 2008/0262313 A1 | | 10/2008 | Shimizu et al. |
| 2008/0267466 A1 | | 10/2008 | Fujita et al. |
| 2009/0326514 A1 | | 12/2009 | Takizawa et al. |

FOREIGN PATENT DOCUMENTS

| | | |
|---|---|---|
| JP | 3-289779 | 12/1991 |
| JP | 4-109927 | 4/1992 |
| JP | 4-180736 | 6/1992 |
| JP | 7289504 | 11/1995 |
| JP | 2001137182 | 5/2001 |
| JP | 2001224551 | 8/2001 |
| JP | 2001224553 | 8/2001 |
| WO | WO 92/21307 | 12/1992 |
| WO | WO 98/11816 | 3/1998 |
| WO | WO 01/08548 | 2/2001 |
| WO | WO 01/35813 | 5/2001 |
| WO | WO 01/50941 | 7/2001 |
| WO | WO 01/65995 | 9/2001 |
| WO | WO 01/87377 | 11/2001 |
| WO | WO 02/067593 | 8/2002 |
| WO | WO 03/009739 | 2/2003 |
| WO | WO 03/010967 | 2/2003 |
| WO | WO 03/011103 | 2/2003 |
| WO | WO 03/028224 | 4/2003 |
| WO | PCT/IL2004/00287 | 3/2004 |

OTHER PUBLICATIONS

Energizer 357/303, Product Datasheet, Form No. EBC 8870EU-A.
Energizer Application Manual, Zinc Air (Zn/O$_2$)—2004 Energizer, pp. 1-4.
Energizer Silver Oxide (Zn/Ag$_2$O), Application Manual, Nov. 6, 2001, pp. 1-5.
Wang et al, "Integrated Micro-Instrumentation for Dynamic Monitoring of the Gastro-Intestinal Tract", Presented at IEEE Instrumentation and Measurement Technology Conference, May 2002, Anchorage, Ak, USA, 222.see.ed.ac.uk/Naa.publications.html.
"Robots for the future" Shin-ichi, et al, Nov. 29, 2001.
"The Radio Pill", Rowlands et al, British Communications and Electronics, Aug. 1960, pp. 598-601.
"Video Camera to "TAKE""—RF System lab, Dec. 25, 2001.
"Wellesley company sends body monitors into space"—Crum, Apr. 1998.
www.nfnorkia.com—NORIKA3 Dec. 24, 2001.
"Wireless transmission of a color television moving image from the stomach using a miniature CCD camera, light source and microwave transmitter". Swain CP, Gong F, Mills TN, Gastrointest Endosc 1997;45;AB40.
BBC News Online—Pill camera to broadcast from the gut, Feb. 21, 2000, www.news.bbc.co.uk.

* cited by examiner

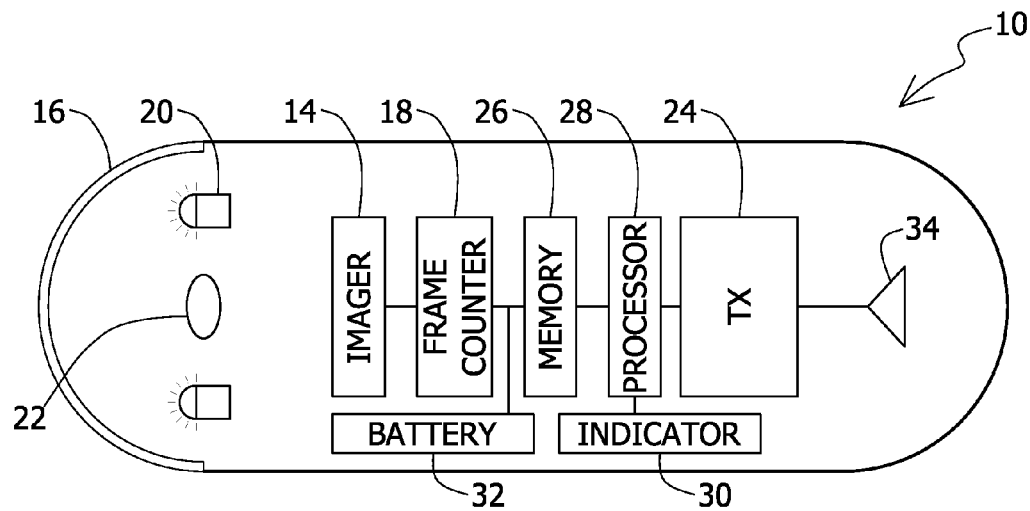
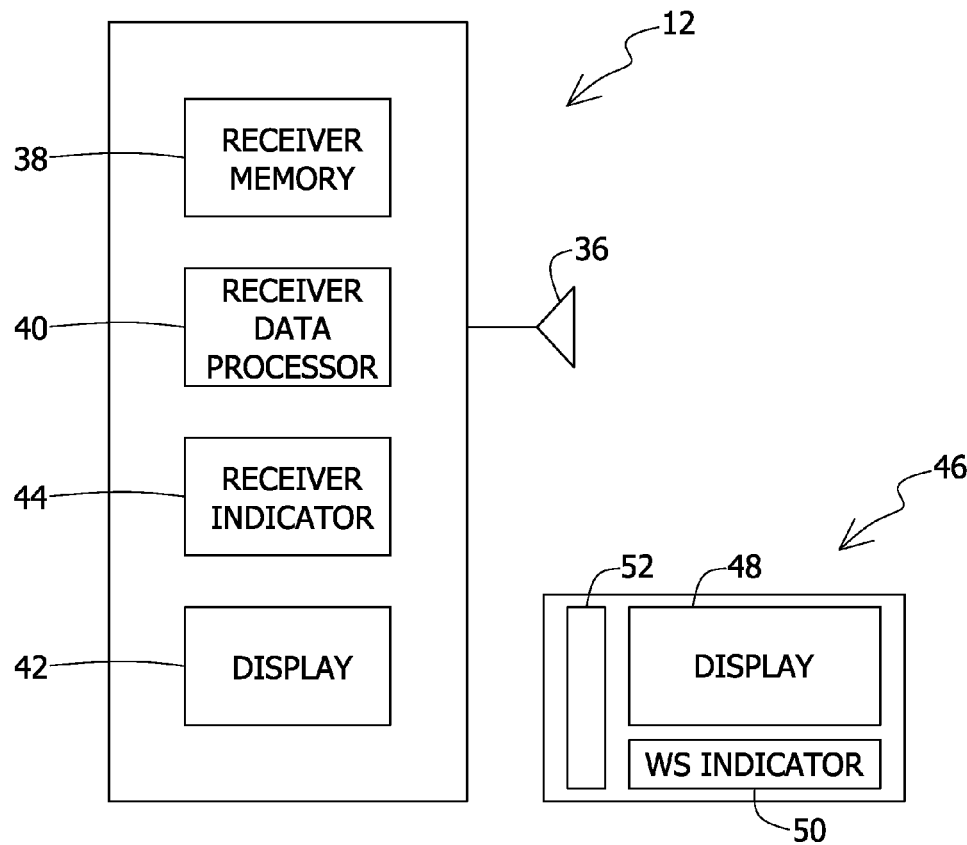

DEVICE AND SYSTEM FOR CHECKING THE STATUS OF AN IN-VIVO IMAGING DEVICE

CROSS REFERENCE TO RELATED APPLICATIONS

This application is a continuation of U.S. patent application Ser. No. 11/723,501, filed Mar. 20, 2007, which claims the benefit of U.S. Ser. No. 60/787,187, filed on Mar. 30, 2006, both of which are hereby incorporated by reference.

FIELD OF THE INVENTION

The present invention relates to a device and a system for checking the status of a battery located in a sensing device in general and an in-vivo imaging device in particular.

BACKGROUND OF THE INVENTION

Such a sensing device may be an in-vivo sensing device, such as a capsule used, for example, for sensing of passages or cavities within a body, and for collecting data (e.g., image data, pH data, temperature information, pressure information), as known in the art. Such sensing devices are generally used in conjunction with other equipment that may include, inter alia, various endoscopic imaging systems and equipment for performing imaging in various internal body cavities. Some such sensing devices transmit the collected data to an external receiving unit.

The in-vivo sensing device may include, for example, an imaging system for obtaining images from inside a body cavity or lumen, such as the gastrointestinal (GI) tract. The imaging system may include, for example, an illumination unit, such as a set of light emitting diodes (LEDs), or other suitable light sources. The device may include an imaging sensor and an optical system, which focuses the images onto the imaging sensor. A transmitter and antenna may be included for transmitting the images signals. Alternatively, a transceiver may be included so that the in-vivo sensing device may receive signals from an external transmitter. An external receiver/recorder, for example worn by the patient, may record transmitted image data and store image and other data. The recorded data may then be downloaded from the receiver/recorder to a computer or workstation for display and analysis.

The transmitter/transceiver and illumination unit of the in-vivo sensing device may be powered by a battery installed therein during production. The production process involves various stages during which the battery may be intentionally or accidentally activated and consequently use some of its power. After production, the device may be stored for a period of time and then shipped to a customer over another period of time. During these periods of time, the battery may also possibly be accidentally activated and therefore use some of its power. The total time for which the battery was in use prior to the device reaching the customer is a measure of the remaining battery life time.

Sensing of passages or cavities within a body may take several hours. Clearly, it is undesirable to use an in-vivo sensing device having a battery that is inoperative, or that may become inoperative before the in-vivo sensing device has completed imaging the required length of passages or cavities within the body that are under inspection. In general, components of the in-vivo sensing device have specified operating voltage ranges. Situations may arise in which the in-vivo sensing device's battery may become defective before use by the patient, or its voltage may not be constant over a required period of time. Therefore, if the voltage of the battery was to fall below a certain critical voltage, some of the components may not function correctly, if at all.

The in-vivo sensing device may be a closed and sealed unit such as an autonomous swallowable capsule in which the battery was installed during production. Therefore, there is a need for a non-invasive method of checking the status of the battery, prior to use.

SUMMARY OF THE INVENTION

In accordance with an embodiment of the present invention, there is provided an in-vivo imaging device powered by a battery, comprising:
  an imager for capturing image frames;
  a frame counter for counting the number of image frames captured; and
  an indicator for indicating a warning if the number of image frames captured exceeds a critical number of frames.

In accordance with some embodiments, the in-vivo imaging device may be a swallowable capsule.

In accordance with some embodiments, the swallowable capsule may be autonomous.

In accordance with another embodiment of the present invention, there is provided an in-vivo imaging system, comprising an in-vivo imaging device and a receiver, the in-vivo imaging device being powered by a battery, the receiver and the in-vivo imaging device being separate physically non-connected members;
  the in-vivo imaging device comprising:
  an imager for capturing image frames;
  a frame counter for counting the number of image frames captured; and
  a transmitter for wirelessly transmitting at least the number of image frames captured;
  the receiver comprising:
  at least one antenna for receiving data transmitted by the in-vivo imaging device;
  a receiver memory for storing data received by the at least one antenna;
  a receiver data processor; and
  a receiver indicator for indicating a warning if the number of image frames counted exceeds a critical number of frames.

In accordance with some embodiments, the transmitter is a radio frequency transmitter.

In accordance with some embodiments, the transmitter transmits, inter alia, image data.

In accordance with some embodiments, the imaging device may be a swallowable capsule and may be autonomous.

In accordance with an embodiment of the present invention, there is provided an in-vivo imaging system, comprising an in-vivo imaging device, a receiver and a workstation, the in-vivo imaging device being powered by a battery, the receiver and the in-vivo imaging device being separate physically non-connected members;
  the in-vivo imaging device comprising:
  an imager for capturing image frames;
  a frame counter for counting the number of image frames captured; and
  a transmitter for wirelessly transmitting at least the number of image frames captured;
  the receiver comprising:

at least one antenna for receiving data transmitted by the in-vivo imaging device; and a receiver memory for storing data received by the at least one antenna;

the workstation comprising a workstation indicator for indicating a warning if the number of image frames captured exceeds a critical number of frames.

If desired, the workstation indicator may be a workstation display screen or a source of light such as a Light Emitting Diode.

There also provided, in accordance with an embodiment of the invention a method for checking the status of an in-vivo imaging device, comprising the steps of:

capturing image frames by an imager located in the in-vivo imaging device;

counting the number of image frames captured; and indicating a warning if the number of image frames captured exceeds a critical number of frames.

In accordance with some embodiments, the warning is indicated by an indicator located in the in-vivo sensing device.

In accordance with other embodiments, the warning is indicated by the in-vivo imaging device shutting down.

In accordance with yet other embodiments, the warning is indicated by the in-vivo imaging device suppressing the operation of illumination sources.

In accordance with another embodiment, there is provided a method for checking the status of an in-vivo imaging device, comprising the steps of:

capturing image frames by an imager located in the in-vivo imaging device; counting the number of image frames captured;

transmitting wirelessly by the in-vivo imaging device the number of image frames;

receiving the number of image frames at a receiver; and indicating a warning by the receiver if the number of image frames exceeds a critical number of frames.

In accordance with yet another embodiment, there is provided a method for checking the status in-vivo imaging device, comprising the steps of:

capturing image frames by an imager located in the in-vivo imaging device;

counting the number of image frames captured;

transmitting wirelessly by the in-vivo imaging device the number of image frames;

receiving the number of image frames at a receiver;

downloading the number of image frames to a work station;

indicating a warning by the workstation if the number of image frames exceeds a critical number of frames.

In accordance with another embodiment, there is provided a method for checking the status of an in-vivo imaging device powered by a battery installed therein, comprising the steps of:

monitoring the battery voltage;

comparing the monitored battery voltage with a critical voltage value;

determining if the monitored battery voltage deviates from the critical voltage value by amounts outside an acceptable limit; and indicating a warning by an indicator located in the in-vivo sensing device, if the monitored battery voltage deviates from the critical voltage value by amounts outside an acceptable limit.

In accordance with another embodiment, there is provided a method for checking the status of an in-vivo imaging device powered by a battery installed therein, comprising the steps of:

monitoring the battery voltage;

transmitting wirelessly by the in-vivo imaging device monitored battery voltage values;

receiving the monitored battery voltage values at a receiver; and comparing at the receiver the monitored battery voltage with a critical voltage value;

determining at the receiver if the monitored battery voltage deviates from the critical voltage value by amounts outside an acceptable limit; and indicating a warning by an indicator located in the receiver, if the monitored battery voltage deviates from the critical voltage value by amounts outside an acceptable limit.

In accordance with yet another embodiment, there is provided a method for checking the status of an in-vivo imaging device powered by a battery installed therein, comprising the steps of:

monitoring the battery voltage;

transmitting wirelessly by the in-vivo imaging device monitored battery voltage values;

receiving the monitored battery voltage values at a receiver;

downloading the received monitored battery voltage values to a workstation;

comparing at the workstation the monitored battery voltage with a critical voltage value;

determining at the workstation if the monitored battery voltage deviates from the critical voltage value by amounts outside an acceptable limit; and indicating a warning by an indicator located in the workstation, if the monitored battery voltage deviates from the critical voltage value by amounts outside an acceptable limit.

Generally, the warning may be a visible signal in the form of a flashing light, or in the form of a written warning on a receiver display, or in the form of an audio signal.

BRIEF DESCRIPTION OF THE DRAWINGS

FIG. 1 shows a schematic diagram of an in vivo imaging system according to an embodiment of the present invention.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

The device, system and method of the present invention may be used with an imaging system or device such as that described in U.S. Pat. No. 5,604,531 entitled "In Vivo Video Camera System," which is incorporated herein by reference. A further example of an imaging system and device with which the system and method of the present invention may be used is described in U.S. Patent Application Publication No. 2001/0035902 entitled "Device and System for In Vivo Imaging," which is hereby incorporated by reference.

Reference is made to FIG. 1, showing a schematic diagram of an in-vivo imaging system according to embodiments of the present invention. The in-vivo imaging system may comprise an in-vivo imaging device 10 and a receiver 12. Typically, the in-vivo imaging device 10 may be a wireless device. In some embodiment, the in-vivo imaging device 10 may be autonomous. In some embodiments, the in-vivo imaging device 10 may be a swallowable capsule for capturing images, for example, images of the gastrointestinal tract of a patient. However, other body lumens or cavities may be imaged or examined with the in-vivo imaging device 10. The in-vivo imaging device 10 may include at least one sensor such as an imager 14 for capturing image frames, a viewing window 16, a frame counter 18 for counting the number of image frames captured by the imager 14, one or more illumination sources 20, an optical system 22, a transmitter 24, a memory 26 a processor 28, an indicator 30 and a battery 32. In some embodiments, the transmitter 24 may be a transceiver, that is transmitter/receiver enabling the in-vivo imaging device 10 to receive data or instructions from an external unit. Such signals may include operational commands to change modes of operation of the in-vivo imaging device 10. The optical system 22 may include, for example, lenses or mirrors, for focusing light onto the imager 14. The imager 14 may be and/or contain a CMOS imager. Alternatively, other imagers may be used, e.g. a CCD imager or other imagers. In some embodiments, the indicator 30 may be a source of light, such as a LED, whereas in other embodiments the indicator 30 may be the illumination sources 20. In accordance with some embodiments, the in-vivo system may comprise and in-vivo sensing device for sensing of passages or cavities within a body, and for collecting data such as, but not limited to, pH data, temperature data and pressure data. Instead of an imager for capturing image frames, the in-vivo sensing device may have a sensor for sensing associated data cycles of the data being collected.

In some embodiments, prior to use by a patient, the in-vivo imaging device 10 is retained in a container in a non-operative state so that no power, or only a negligibly small amount of power, is withdrawn from the battery 32. According to one embodiment when the in-vivo imaging device 10 is removed from the container, prior to use, it becomes operative. According to another embodiment, the in-vivo imaging device is activated, i.e. made operative, by other means, prior to use by a patient. Under certain circumstances the in-vivo imaging device 10 may become operative for certain periods of time prior to it being used by a patient. That is, even before reaching the patient. This may happen during production either intentionally in order to check the in-vivo imaging device 10 or accidentally. This may also possibly happen during transportation and possibly during storage of the in-vivo imaging device 10. When the in-vivo imaging device 10 is operative it draws power from the battery 32 to operate, inter alia, the illumination sources 20, the imager 14 as it captures image frames and the transmitter as it transmits, inter alia, image frame data captured by the imager 14. The number of image frames captured by the imager 14 may be representative of the time during which the in-vivo imaging device 10 was operative. Consequently, the number of image frames captured by the imager 14 and transmitted by the in-vivo imaging device 10 prior to it being used by the patient may be indicative of the effective remaining lifetime of the battery.

In some embodiments, if the number of image frames captured and registered by the processor, prior to use of the in-vivo imaging device 10 by a patient, exceeds a critical number of frames, the battery lifetime is determined to be faulty and a faulty battery lifetime indication is generated. If $T1$ is the lifetime in seconds of an unused battery, $T2$ is the time in seconds that the battery was in use before the in-vivo imaging device 10 reached the patient, and $T3$ is the time required for sensing passages or cavities within the body of the patient; then $T1-T2=T4$ is the remaining lifetime of the battery and clearly $T4$ has to be greater than $T3$. If the time, $T2$, that the battery was in use before the in-vivo imaging device 10 reached the patient, reaches a critical value TC for which $T4$ is not greater than $T3$, and the imager 14 captures images at a rate of N frames per second, then the critical number of frames is $N \times T2$. In a nonbinding example, if the imager 14 captures images at a rate of 2 frames per second and it is determined that TC=10 minutes, then the critical number of frames is 1200.

The indicator 30 may indicate a warning that the effective remaining lifetime of the battery 32 is low, that is, lower than the battery lifetime necessary for the in-vivo imaging device to complete imaging the required length of passages or cavities within the body that are under inspection. The indicator 30 may be an auxiliary source of light, such as a LED, and the warning may be a flashing of the auxiliary source of light, flashing on and off. In other embodiments, the warning may be indicated by the illumination sources 20 flashing on and off at a given frequency different to the flashing on and off frequency used when capturing image frames.

The transmitter 24 may transmit data, for example, via an antenna 34. Such data may include for example, image data and possibly the number of image frames captured by the imager 14 and possibly other data. The transmitted data may be received by the receiver 12 which is located outside the patient's body, for example, via a receiver antenna 36 or antenna array.

According to one embodiment, the receiver 12 preferably includes a receiver memory 38, for storing data transmitted by the in-vivo imaging device 10 and a receiver processor 40 for processing at least partially the received data. The receiver 12 may include a display 42, for displaying, inter alia, the image data received from the in-vivo imaging device 10. The receiver 12 may also include a receiver indicator 44 which may issue a warning that the battery power of the in-vivo imaging device's battery 32 is low. In some embodiments, the receiver 12 may also include a transmitter enabling it to transmit data or instructions to the in-vivo imaging device 10 via a transmitter antenna.

In some embodiments, when the in-vivo imaging device 10 is activated, prior to being used by a patient, the number of image frames captured by the imager 14 of the in-vivo imaging device 10, due to intentional or unintentional operation of the in-vivo imaging device 10, may be transmitted by the transmitter 24 and received by the receiver 12. If the receiver processor 40 determines that the received number of image frames exceeds the critical number of frames, the receiver 12 may issue a warning. The warning issued by the receiver 12 may be issued in different forms, depending on the nature of the receiver indicator 44. In some embodiments, the receiver indicator may be a source of light, such as a LED and the warning issued may be a visual signal, for example, in the form of a flashing on and off of the receiver indicator 44. Alternatively, the receiver indicator 44 may be an LCD display, or the like, and the warning issued may be visual signal in the form of an appropriate written warning message indicating that the battery power of the battery 32 may be low. In some embodiments, the receiver indicator 44 may be a loudspeaker, and the warning issued may be an audio signal. In other embodiments, the receiver indicator may be both a loudspeaker and a visual member, so that the warning issued may be either or both audio and visual. The warning issued by the receiver indicator 44 may be in addition to, or instead of, a warning issued by the in-vivo imaging device's indicator 30. In some embodiments, if the receiver processor 40 determines that the received number of image frames exceeds the critical number of frames, the receiver 12 may transmit to the in-vivo imaging device 10 an appropriate signal, indicating that the received number of image frames exceeds the critical number of frames as a result of which a warning is issued by the in-vivo imaging device's indicator 30. In some embodiments, if the receiver processor 40 determines that the received number of image frames exceeds the critical number of frames the in-vivo imaging system electrically shuts down. In such embodiments, inadvertent use of the in-vivo imaging device 10 is prevented. The system shut down may be a shut down of the in-vivo imaging device 10 or of the receiver 12, or of both the in-vivo imaging device 10 and the receiver 12.

Situations may arise in which the in-vivo imaging device's battery 32 may become defective, or its voltage may not be constant over a required period of time. In such cases, the voltage status of the battery 32 may be such that the in-vivo imaging device may not function properly, independent of whether or not the number of image frames captured by the imager 14 exceeds the critical number of frames prior to use of the in-vivo imaging device 10 by the patient.

Prior to use of the in-vivo imaging device 10 the battery voltage may be monitored and may be compared with a critical voltage value in the in-vivo imaging device 10 to determine if it substantially deviates from that value as a function of time. If, prior to use, the monitored battery voltage is determined to deviate from the critical voltage value as a function of time by amounts outside an acceptable limit, then the battery voltage is determined to be faulty and a faulty battery voltage indication is generated. In accordance with some embodiments, on activating the in-vivo imaging device 10, the indicator 30 may indicate a warning. In accordance with other embodiments, on activating the in-vivo imaging device 10, the faulty battery voltage indication may be transmitted to the receiver 12 and the receiver indicator 44 may indicate a warning. In accordance with yet other embodiments, on activating the in-vivo imaging device 10, monitored voltage values may be transmitted to the receiver 12 and may be compared with a critical voltage value in the receiver 12 to determine if they deviate from that value as a function of time by amounts outside an acceptable limit. If, prior to use, the monitored battery voltage is determined to deviate from the critical voltage value as a function of time by amounts outside an acceptable limit, then the receiver indicator 44 may indicate a warning.

In accordance with some embodiments, the number of images frames and the monitored battery voltage received by the receiver 12 may be downloaded from the receiver 12 to a workstation 46 that includes a workstation display 48, a workstation indicator 50 and a workstation processor 52. Determining if the battery has a faulty lifetime and/or a faulty voltage, may be performed at the workstation 46 by the workstation processor 52. If either or both of the two faulty battery conditions is determined to exist then appropriate warning may be indicated by the work station 46, either on the workstation display 48 or by the workstation indicator 50. The warning on the workstation display 48 may be in the form of a written warning. The workstation indicator 50 may be a source of light, such as a LED, for generating a visible warning signal and/or a source of sound, such as a loudspeaker, for generating an audio warning signal. In some embodiments, if it is determined by the workstation processor 52 that either or both of the two faulty battery conditions is determined to exist, the workstation may instruct the receiver 12 to transmit to the in-vivo imaging device 10 an appropriate signal, indicating the existence of a faulty battery condition, as a result of which a warning is issued by the in-vivo imaging device's indicator 30.

Accordingly, if on activating the in-vivo imaging device 10, prior to use by a patient, the battery is determined to be faulty, either by having a low effective remaining lifetime or by having unacceptable voltage characteristics, the patient will be warned of the situation and may decide not swallow the in-vivo imaging device 10.

In some embodiments, if on activating the in-vivo imaging device 10, prior to use by a patient, the battery is determined to be faulty, either by having a low effective remaining lifetime or by having unacceptable voltage characteristics, the in-vivo imaging system electrically shuts down. In such embodiments, inadvertent use of the faulty in-vivo imaging device 10 is prevented. The system shut down may be a shut down of the in-vivo imaging device 10 or of the receiver 12, or of both the in-vivo imaging device 10 and the receiver 12.

It will be appreciated by persons skilled in the art that the present invention is not limited to what has been particularly shown and described hereinabove. Alternate embodiments are contemplated which fall within the scope of the invention.

The invention claimed is:

1. A swallowable in-vivo imaging device, comprising:
   an imager for capturing image frames;
   a battery to power said in-vivo imaging device;
   a frame counter for counting image frames captured by said imager;
   an indicator configured to indicate a warning prior to swallowing of the in-vivo imaging device, wherein the indicator is at least one of a light source to issue a visual signal and a loudspeaker to issue an audio signal;
   a memory; and
   a processor configured to register captured image frames and cause said indicator to indicate the warning when a number of image frames counted by the frame counter prior to swallowing of the in-vivo imaging device exceeds a critical number of frames;
   wherein the critical number of frames is calculated based on a lifetime of the battery, an amount of time necessary to complete imaging of a required length of a gastrointestinal tract, and an image frame capture rate of the imager, and
   wherein a difference between the lifetime of the battery and a division of the critical number of frames by the image frame capture rate is greater than the amount of time necessary to complete imaging of the required length of the gastrointestinal tract.

2. The in-vivo imaging device according to claim 1, comprising a swallowable capsule.

3. The in-vivo imaging device according to claim 2, wherein the swallowable capsule is autonomous.

4. An in-vivo imaging system, comprising an in-vivo imaging device and a receiver, the in-vivo imaging device being powered by a battery, the receiver and the in-vivo imaging device being separate physically non-connected members, the in-vivo imaging device comprising:
- an imager for capturing image frames;
- a frame counter for counting a number of image frames captured by said imager;
- an indicator configured to indicate a warning prior to swallowing of the in-vivo imaging device, wherein the indicator is at least one of a light source to issue a visual signal and a loudspeaker to issue an audio signal; and
- a transmitter for wirelessly transmitting at least the number of image frames captured by said imager;

the receiver comprising:
- at least one antenna for receiving data transmitted by the in-vivo imaging device;
- a receiver memory for storing data received by the at least one antenna;
- a receiver data processor; and
- a receiver indicator configured for indicating the warning prior to swallowing of the in-vivo imaging device if a number of image frames counted by said frame counter exceeds a critical number of frames, wherein the critical number of frames is calculated based on a lifetime of the battery, an amount of time necessary to complete imaging of a required length of a gastrointestinal tract, and an image frame capture rate of the imager, and wherein a difference between the lifetime of the battery and a division of the critical number of frames by the image frame capture rate is greater than the amount of time necessary to complete imaging of the required length of the gastrointestinal tract.

5. The in-vivo imaging system according to claim 4, wherein the transmitter is a radio frequency transmitter.

6. The in-vivo imaging system according to claim 5, wherein the transmitter transmits image data.

7. The in-vivo imaging system according to claim 4, wherein the imaging device is a swallowable capsule.

8. The in-vivo imaging system according to claim 7, wherein the swallowable capsule is autonomous.

* * * * *